United States Patent
Chung (10) Patent No.: US 11,920,124 B2
(45) Date of Patent: Mar. 5, 2024

(54) METHOD OF PRODUCING LACTIC ACID BACTERIA DUAL-COATED WITH PROTEIN AND POLYSACCHARIDE BY USING PROTEIN HYDROLYSATE

(71) Applicant: CELL BIOTECH CO., LTD., Gyeonggi-do (KR)

(72) Inventor: Myung Jun Chung, Seoul (KR)

(73) Assignee: CELL BIOTECH CO., LTD., Gyeonggi-do (KR)

(*) Notice: Subject to any disclaimer, the term of this patent is extended or adjusted under 35 U.S.C. 154(b) by 263 days.

(21) Appl. No.: 16/839,289

(22) Filed: Apr. 3, 2020

(65) Prior Publication Data
US 2020/0325439 A1    Oct. 15, 2020

(30) Foreign Application Priority Data
Apr. 15, 2019    (KR) .................. 10-2019-0043610

(51) Int. Cl.
| | |
|---|---|
| C12N 1/20 | (2006.01) |
| A23J 3/34 | (2006.01) |
| A23L 3/44 | (2006.01) |
| A23L 33/125 | (2016.01) |
| A23L 33/135 | (2016.01) |
| A23L 33/18 | (2016.01) |
| A23L 33/185 | (2016.01) |
| A23L 33/19 | (2016.01) |
| A23P 20/10 | (2016.01) |
| C12N 1/04 | (2006.01) |
| C12P 21/06 | (2006.01) |

(52) U.S. Cl.
CPC ............... *C12N 1/20* (2013.01); *A23J 3/344* (2013.01); *A23J 3/346* (2013.01); *A23L 3/44* (2013.01); *A23L 33/125* (2016.08); *A23L 33/135* (2016.08); *A23L 33/18* (2016.08); *A23L 33/185* (2016.08); *A23L 33/19* (2016.08); *A23P 20/10* (2016.08); *C12N 1/04* (2013.01); *C12P 21/06* (2013.01); *A23V 2002/00* (2013.01); *A23V 2400/113* (2023.08); *A23V 2400/249* (2023.08); *A23V 2400/519* (2023.08)

(58) Field of Classification Search
None
See application file for complete search history.

(56) References Cited

U.S. PATENT DOCUMENTS

| | | | | |
|---|---|---|---|---|
| 3,716,456 | A | * 2/1973 | Weetall | G01N 33/182 |
| | | | | 435/808 |
| 2014/0093613 | A1 | 4/2014 | Cevallos et al. | |
| 2015/0152378 | A1 | 6/2015 | Chung et al. | |

FOREIGN PATENT DOCUMENTS

| | | | |
|---|---|---|---|
| CN | 102573862 A | 7/2012 | |
| EP | 0087247 B1 | * 5/1986 | |
| JP | H0656680 A | 3/1994 | |
| JP | 2002-320473 A | 11/2002 | |
| JP | 2008-516591 A | 5/2008 | |
| JP | 2009-011227 A | 1/2009 | |
| KR | 10-2002-0069862 A | 9/2002 | |
| KR | 10-2002-0069863 A | 9/2002 | |
| KR | 10-0437984 B1 | 9/2004 | |
| KR | 10-2013-0067682 A | 6/2013 | |
| KR | 10-1698379 B1 | 1/2017 | |
| KR | 10-2017-0032136 A | 3/2017 | |
| KR | 10-2017-0072825 A | 6/2017 | |
| KR | 10-2018-0114268 A | 10/2018 | |
| WO | WO-2006/093022 A1 | 9/2006 | |
| WO | WO-2009/069498 A1 | 6/2009 | |
| WO | WO-2018224035 A1 | * 12/2018 | ............... A23J 3/34 |

OTHER PUBLICATIONS

Davenport et al. Moj Food Process Technol. 2016 2(2): 67-72.*
Shu et al. Biomolecules 2018, 8, 101, pp. 1-8.*
Doherty, et al. (2010) "Efficacy of whey protein gel networks as potential viability-enhancing scaffolds for cell immobilization of *Lactobacillus rhamnosus* GG.", *Journal of Microbiological Methods*, 80(3):231-241.
Extended European Search Report, dated Jul. 22, 2020, issued in European Patent Application No. 20169113.6.
Office Action from corresponding Chinese Patent Application No. 202010276535.7, dated Mar. 16, 2023.

* cited by examiner

*Primary Examiner* — Oluwatosin A Ogunbiyi
(74) *Attorney, Agent, or Firm* — Harness, Dickey & Pierce, P.L.C.

(57) ABSTRACT

The present disclosure relates to a method of producing lactic acid bacteria dual-coated with protein and polysaccharide by using a protein hydrolysate, and lactic acid bacteria having a dual coating, produced by the method. The lactic acid bacteria having a dual coating of protein and polysaccharide, produced according to the present disclosure, have very excellent dry-freezing viability, acid resistance and bile resistance. Accordingly, the lactic acid bacteria having a dual coating of protein and polysaccharide according to the present disclosure will be very useful for the production of fermented milk, processed milk, fermented soy products, processed foods, functional beverages, functional foods, common foods, etc.

5 Claims, 5 Drawing Sheets

Inside and outside photographs of dual-coated *Streptococcus thermophilus* CBT ST3

10,000 X inside photograph 10,000 X inside photograph 10,000 X outside photograph

FIG. 4

Inside and outside photographs of dual-coated *Bifidobacterium breve* CBT BR3

10,000 X inside photograph

10,000 X inside photograph

10,000 X outside photograph

FIG. 5

Photographs of non-coated and dual-coated *Lactobacillus acidophilus* CBT LA1

10,000 X (non-coated)

10,000 X (coated, inside)

10,000 X (coated, outside)

FIG. 6

METHOD OF PRODUCING LACTIC ACID BACTERIA DUAL-COATED WITH PROTEIN AND POLYSACCHARIDE BY USING PROTEIN HYDROLYSATE

CROSS-REFERENCE TO RELATED APPLICATION

This application claims priority to Korean Patent Application No. 10-2019-0043610, filed on Apr. 15, 2018, the disclosure of which is incorporated herein by reference in its entirety.

FIELD

The present disclosure relates to a method of producing lactic acid bacteria dual-coated with protein and polysaccharide by using a protein hydrolysate, and lactic acid bacteria having a dual-coating, produced by the method.

BACKGROUND

Lactic acid bacteria, also known as *Lactobacillus*, are important bacteria that live in mammalian intestines and are also used as probiotics that prevent abnormal fermentation caused by various bacteria. For example, *Lactobacillus bulgaricus* is a lactic acid bacterium known for the longest time and is used in the manufacture of yogurt and also used as a starter in the manufacture of cheese or fermented butter. In addition, aerobic *Lactobacillus acidophilus* is present in the intestines of humans, all mammals and other animals, and is used in the production of butter or milk or for the treatment of intestinal auto-intoxication. In addition, *Lactobacillus lactis* is the most important dairy lactic acid bacterium that produces DL-lactic acid, which is always present in milk and used in butter or cheese production.

The useful lactic acid bacteria as described above are colonize in the intestines and activate intestinal movement, thus ameliorating constipation or diarrhea and facilitating bowel movement. In addition, these lactic acid bacteria exhibit various physiological activities, including immune enhancement, anti-hyperlipidemia, anti-atopy, diet, anti-diabetic, and anticancer activities, and thus are widely used in health functional foods, probiotic drugs, skin improvement cosmetics, feed additives, and so on. However, in order to exhibit the above-described physiological effects, the lactic acid bacteria should be ingested in amounts that are much larger than the amounts of the lactic acid bacteria contained in conventional foods such as yogurt. Therefore, a method of separating only lactic acid bacteria and taking the separated lactic acid bacteria easily in the form of powder or capsules has been popularized.

Since these lactic acid bacteria are based on live bacteria themselves, unlike other industrial microorganisms that mainly based on fermentation products, maintaining the viability of these lactic acid bacteria during their distribution period and their ingestion is a very important challenge. That is, when the lactic acid bacteria are ingested orally as probiotics themselves, problems arise in that their growth in the human body is inhibited by digestive enzymes and bile acids secreted from the stomach with a pH of 3 or less and the small intestine, and thus the number of live bacteria that reach the large intestine decreases and the intestinal colonization rate of the lactic acid bacteria also decreases.

For this reason, the lactic acid bacteria are considerably unstable and the long-term storage and use thereof is significantly limited, even though these lactic bacteria are very beneficial in terms of their usefulness and value. Fermented milk products and probiotics based on these lactic acid bacteria show a significant decrease in lactic acid bacteria viability due to oxygen or oxidative stress during the production and storage thereof, and this decrease hinders the industrial use thereof or the exhibition of the effect thereof after oral ingestion.

In an attempt to solve the above-described problems, various methods of coating lactic acid bacteria have been developed. In the initial stage, there were enteric-coating capsulation and microencapsulation with gelatin, polysaccharides, gums, etc., but the use of expensive coating agents or additional processes has been pointed out as a problem.

In an attempt to solve this problem, the following methods have been competitively developed: a method for producing a double-structured jelly containing a high concentration of live lactic acid bacteria; a method of forming a quadruple coating by adding a water-soluble polymer, hyaluronic acid, a coating agent having porous particles, and a protein (Korean Patent Application No. 10-2011-0134486); a method of forming a quadruple coating using a water-soluble polymer, a functional hydrated hyaluronic acid, porous particles, and a protein (Korean Patent Application No. 10-2015-0129986); a method of coating lactic acid bacteria with casein, a coating agent, edible oil and fat, a *Lactobacillus plantarum* extracellular polymeric substance, and alginic acid to improve the intestinal viability of the lactic acid bacteria (Korean Patent Application No. 10-2016-0172568); and a method of coating with silk fibroin to improve intestinal colonization (Korean Patent Application No. 10-2017-0045326).

However, these improved lactic acid bacteria coating technologies also problems in that they cannot completely coat the surface of lactic acid bacteria, and thus the lactic acid bacteria are still insufficient in terms of their freeze-drying viability, heat resistance, acid resistance, bile resistance, intestinal colonization ability, etc., and the viability thereof during storage and distribution is insufficient.

The patent documents and references mentioned in the present specification are incorporated herein by reference to the same extent as if each reference is individually and clearly specified by reference.

PRIOR ART DOCUMENTS

Patent Documents

Korean Patent Application No. 10-2011-0134486;
Korean Patent Application No. 10-2015-0129986;
Korean Patent Application No. 10-2016-0172568;
Korean Patent Application No. 10-2017-0045326.

SUMMARY

The present inventors have made extensive research efforts to develop a lactic acid bacteria coating method capable of improving the freeze-drying viability, storage stability, acid resistance and bile resistance of lactic acid bacteria, and as a result, have experimentally found that, when a protein is hydrolyzed and lactic acid bacteria are dual-coated with the hydrolyzed protein along with a polysaccharide and a cryoprotectant, the freeze-drying viability, acid resistance and bile resistance of the lactic acid bacteria can be greatly improved, thereby completing the present disclosure.

Therefore, it is an object of the present disclosure to provide a method of effectively dual-coating lactic acid bacteria using a hydrolyzed protein so as to improve the freeze-drying viability, storage stability, acid resistance and bile resistance of the lactic acid bacteria.

Another object of the present disclosure is to provide lactic acid bacteria having improved freeze-drying viability, storage stability, acid resistance and bile resistance due to a dual-coating formed thereon.

Still another object of the present disclosure is to provide a food composition including the dual-coated lactic acid bacteria.

Other objects and technical features of the present disclosure will be disclosed in more detail with reference to the following description of the disclosure, the appended claims and the accompanying drawings.

In accordance with one aspect of the present disclosure, there is provided a method for producing lactic acid bacteria having a dual-coating of protein and polysaccharide coatings, the method including the steps of:
(a) treating an aqueous protein solution with a protease, thereby preparing an aqueous protein hydrolysate solution having a protein hydrolysis rate of 45% to 95%;
(b) adding a sugar component and a nitrogen source component for lactic acid bacteria culture to the prepared aqueous protein hydrolysate solution, followed by sterilization, and then inoculating and culturing lactic acid bacteria in the sterilized aqueous solution;
(c) recovering lactic acid bacteria cells from a fermented lactic acid bacteria culture obtained by the culturing;
(d) adding an aqueous cryoprotectant solution and an aqueous polysaccharide solution to the recovered lactic acid bacteria cells, followed by mixing and homogenization; and
(e) freeze-drying the homogenized aqueous lactic acid bacteria cell solution.

Preparation of Protein Hydrolysate

In the present disclosure, the protein that is used for coating of lactic acid bacteria is used after hydrolytic treatment.

According to one embodiment of the present disclosure, hydrolytic treatment of the protein may be performed by adding a protease to an aqueous protein solution containing the protein, and then subjecting the aqueous protein solution to a hydrolysis reaction.

According to one embodiment of the present disclosure, the hydrolysis rate of the protein is preferably in the range of 45% to 95%.

In the present disclosure, the hydrolysis rate of the protein refers to the degree to which the protein was hydrolyzed by the enzyme. The hydrolysis rate of the protein may be calculated by: i) a method of measuring the difference in optical density of the aqueous protein solution between before and after enzymatic hydrolytic treatment; ii) a method of measuring the difference in weight of a precipitate, obtained by centrifuging the aqueous protein solution, between before and after enzymatic hydrolytic treatment; or iii) the average value of the values obtained using the two methods.

According to one embodiment of the present disclosure, the hydrolysis rate of the protein in the present disclosure is a percentage value (%) obtained by dividing a $\Delta$OD value, which is a difference between the optical density (OD) value ("start-point OD") of the aqueous protein solution, measured before treatment with the protease, and the optical density (OD) value ("endpoint OD") of the aqueous protein solution, measured after treatment with the protease, by the start-point OD value. That is, the hydrolysis rate of the protein may be calculated by the following equation:

hydrolysis rate (%)=[$\Delta$OD]/[start-point OD]×100.

According to one embodiment of the present disclosure, the hydrolysis rate of the protein in the present disclosure is a percentage value (%) obtained by dividing a $\Delta$ppt value, which is a difference between the measured weight value ("start-point ppt") of a precipitate, obtained by centrifuging the aqueous protein solution before treatment with the protease, and the measured weight value ("endpoint ppt") of a precipitate, obtained by centrifuging the aqueous protein solution after treatment with the protease, by the start-point ppt value. That is, the hydrolysis rate of the protein may be calculated by the following equation: hydrolysis rate (%)= [$\Delta$ppt]/[start-point ppt]×100.

According to one embodiment of the present disclosure, the average value of the hydrolysis rates measured by the two methods may be used.

According to one embodiment of the present disclosure, the protein that is used for lactic acid bacteria coating may be skim milk powder, isolated soy protein (ISP), or a mixture of skim milk powder and isolated soy protein (ISP).

According to one embodiment of the present disclosure, the hydrolysis rate of skim milk powder in the present disclosure may be 59% to 93%, preferably 75% to 92%, more preferably 80% to 90%.

According to one embodiment of the present disclosure, the hydrolysis rate of isolated soy protein in the present disclosure may be 45% to 86%, preferably 61% to 80%, more preferably 70% to 80%.

According to one embodiment of the present disclosure, the hydrolysis rate of a mixture of skim milk powder and isolated soy protein in the present disclosure may be 75% to 93%, preferably 76% to 85%, and more preferably 78% to 83%.

As used herein, the term "protease" refers to an enzyme that grades the proteins into amino acids or peptide fragments. The protease that is used in the present disclosure may be selected from among commercially available Alcalase, Flavourzyme, Neutrase, Protamax, and the like, but are not limited thereto.

It is presumed that hydrolytic treatment of the protein in the present disclosure produces a water-semisoluble peptide. The water semisoluble peptide refers to a peptide that remains without being completely hydrolyzed into amino acids upon hydrolytic treatment of the protein. In the method of the present disclosure, as the hydrolysis rate increases, the amount of the water semisoluble peptide decreases, and as the hydrolysis rate decreases, the amount of water semisoluble peptide increases. The water semisoluble peptide functions to increase freeze-drying viability by alleviating protein denaturation caused by a physical impact which is applied to the cells during freeze drying. However, if the water-semisoluble peptide is present in excessive amounts in the aqueous protein hydrolysate solution, the culture may change to a hydrophobic state, thereby inducing agglomeration of the lactic acid bacteria and suppressing the culturability of the lactic acid bacteria.

Accordingly, if the hydrolysis rate of the protein in the present disclosure is lower than the lower limit of the above-described range, problems arise in that the hydrophobicity of the culture is increased by a large amount of the non-hydrolyzed water-semisoluble peptide, and thus the lactic acid bacteria agglomerate and are not easily divided, resulting in deterioration in the culturability of the lactic acid bacteria. On the contrary, if the hydrolysis rate of the protein is higher than the upper limit of the above-described range, a problem arises in that the non-hydrolyzed water-semisoluble peptide is present in insufficient amounts, and thus cannot sufficiently alleviate protein denaturation caused by a physical impact which is applied to the lactic acid bacteria during freezes drying, resulting in a decrease in freeze-drying viability.

According to one embodiment of the present disclosure, the concentration of skim milk powder in an aqueous skim milk powder solution during hydrolysis of the skim milk powder may be 0.5 to 10.0 wt %, preferably 1.0 to 6.0 wt %, and the concentration of the protease in the aqueous skim milk powder solution may be 0.0005 to 0.010 wt %, preferably 0.001 to 0.008 wt %.

According to one embodiment of the present disclosure, the concentration of isolated soy protein (ISP) in an aqueous isolated soy protein solution during hydrolysis of the isolated soy protein may be 0.10 to 3.0 wt %, preferably 0.15 to 1.0 wt %, and the concentration of the protease in the aqueous isolated soy protein solution may be 0.001 to 0.10 wt %, preferably 0.005 to 0.030 wt %.

According to one embodiment of the present disclosure, the concentration of a mixture of skim milk powder and isolated soy protein in an aqueous solution of the mixture of skim milk powder and isolated soy protein during hydrolysis of the mixture of skim milk powder and isolated soy protein may be 0.05 to 2.0 wt %, preferably 0.10 to 0.40 wt %, and the concentration of the protease in the aqueous solution of the mixture of skim milk powder and isolated soy protein may be 0.05 to 4.0 wt %, preferably 0.5 to 3.0 wt %.

Lactic Acid Bacteria Culture and Protein Coating

Sugar and nitrogen source components for lactic acid bacteria culture are added to the prepared aqueous protein hydrolysate solution which is then sterilized. Next, lactic acid bacteria are inoculated and cultured in the sterilized aqueous solution.

In the present disclosure, the lactic acid bacteria to be coated are lactic acid bacteria that produce an acid and can proliferate even under weakly acidic conditions, but are not limited thereto. Specifically, the lactic acid bacteria may be one or more of *Lactobacillus* sp., *Bifidobacterium* sp., *Streptococcus* sp., *Lactococcus* sp., *Enterococcus* sp., *Pediococcus* sp., *Leuconostoc* sp., and *Weissella* sp. Preferably, the lactic acid bacteria may be one or more selected from the group consisting of *Lactobacillus plantarum*, *Lactobacillus casei*, *Lactobacillus rhamnosus*, *Lactobacillus alimentarius*, *Lactobacillus sakei*, *Lactobacillus acidophilus*, *Lactobacillus gasseri*, *Lactobacillus delbrueckii*, *Lactobacillus fermentum*, *Lactobacillus bulgaricus*, *Leuconostoc mesenteroides*, *Enterococcus faecium*, *Enterococcus faecalis*, *Streptococcus thermophilus*, *Streptococcus lactis*, *Streptococcus faecalis*, *Bifidobacterium infantis*, *Bifidobacterium bifidum*, *Bifidobacterium longum*, *Bifidobacterium breve*, and *Lactococcus lactis* subsp. *lactis*.

In addition, in the present disclosure, the lactic acid bacteria may preferably be one or more selected from the group consisting of *Lactobacillus plantarum* CBT-LP (accession number: KCTC 10782BP), *Lactobacillus delbrueckii* sub. sp. *bulgaricus* CBT-LG (accession number: KCTC 11864BP), *Lactobacillus acidophilus* CBT-LA (accession number: KCTC 11906BP), *Lactobacillus rhamnosus* CBT-LR (accession number: KCTC 12202BP), *Lactobacillus reuteri* CBT-LU (accession number: KCTC 12397BP), *Lactobacillus casei* CBT-LC (accession number: KCTC 12398BP), *Lactobacillus paracasei* CBT-LPC (accession number: KCTC 12451BP), *Lactobacillus helveticus* CBT-LH (accession number: KCTC 12670BP), *Bifidobacterium infantis* CBT-BT (accession number: KCTC 11859BP), *Bifidobacterium lactis* CBT-BL (accession number: KCTC 11904BP), *Bifidobacterium bifidum* CBT-BF (accession number: KCTC 12199BP), *Bifidobacterium longum* CBT-BG (accession number: KCTC 12200BP), *Bifidobacterium breve* CBT-BR (accession number: KCTC 12201BP), *Pediococcus pentosaseus* CBT-PP (accession number: KCTC 10297BP), *Lactococcus lactis* sub sp. *lactis* CBT-SL (accession number: KCTC 11865BP), *Streptococcus thermophilus* CBT-ST (accession number: KCTC 11870BP), *Enterococcus faecalis* CBT-EFL (accession number: KCTC 12394BP), and *Enterococcus faecium* CBT-EF (accession number: KCTC 12450BP). Preferably, the lactic acid bacteria may be one or more selected from the group consisting of *Lactobacillus acidophilus* CBT-LA, *Lactobacillus plantarum* CBT-LP, *Streptococcus thermophilus* CBT-ST, *Enterococcus faecium* CBT-EF, and *Bifidobacterium longum* CBT-BG, and may more preferably be *Streptococcus thermophilus* CBT-ST, *Bifidobacterium breve* CBT-BR, or *Lactobacillus acidophilus* CBT-LA.

In the present disclosure, as lactic acid bacteria to be coated, any raw material may be used without limitation on its formulation or preparation method, as long as it includes live lactic acid bacteria. However, a culture of lactic acid bacteria may preferably be used.

In the present disclosure, lactic acid bacteria culture conditions for obtaining the culture of lactic acid bacteria are also not particularly limited, and any conditions may be used without limitation as long as they are conditions that are generally used for lactic acid bacteria culture in the art. For example, the lactic acid bacteria may be inoculated in medium, such as MRS, BL, M17, NB or BHI, and cultured at a temperature of 35 to 40° C. under anaerobic conditions substituted with nitrogen gas or carbon dioxide gas for 6 to 48 hours.

In the present disclosure, as the sugar component for lactic acid bacteria culture, there may be used mixed lactose, fructose, sucrose or glucose. Preferably, the sugar component may be selected depending on the characteristics of the strain and used.

In the present disclosure, as the nitrogen source component for lactic acid bacteria culture, yeast extract or soy peptone may be used, but is not limited thereto.

In addition, for lactic acid bacteria culture, trace components may further be added, such as potassium phosphate dibasic, magnesium sulfate, manganese sulfate, calcium chloride, potassium citrate, sodium acetate, L-ascorbic acid, L-glutamic acid, L-cysteine hydrochloride, polysorbate 80, etc.

Recovery and Concentration of Lactic Acid Bacteria Cells

A filtrate is removed as much as possible from a culture obtained by culturing the lactic acid bacteria, and the remaining lactic acid bacteria cell mass as a solid is concentrated to have high specific gravity. The densely concentrated lactic acid bacteria cell mass has the following advantages in the preparation of freeze-dried lactic acid bacteria: i) the amount of cell mass dispensed per tray decreases and the amount of water to be evaporated is also small; ii) the freezing rate is high due to water discharge caused by an osmotic pressure difference in a freezing process; iii) ice crystals are small and uniform and a change in cell morphology is also small, and thus damage to the lactic acid bacteria cell membrane during freezing is also small; and iv) modification of the lactic acid bacteria in a freezing process also less occurs.

In the present disclosure, the method of recovering and concentrating the lactic acid bacteria cells is not particularly limited, but the lactic acid bacteria cells may preferably be recovered and concentrated by a centrifugation method. For example, the lactic acid bacteria cells may be concentrated using a disc type high-speed centrifuge or tubular type high-speed centrifuge, but are not limited thereto.

Addition of Cryoprotectant

In the method of the present disclosure, the storage stability of the lactic acid bacteria may be improved by freeze-drying the lactic acid bacteria. For freeze-drying treatment, a cryoprotectant is added to the recovered and concentrated lactic acid bacteria cells, and then mixed and homogenized. Preferably, an aqueous cryoprotectant solution containing a cryoprotectant may be used.

A cryoprotectant that may be used in the method of the present disclosure may be one or a mixture of two or more selected from the group consisting of trehalose, maltodextrin, mannitol, and skim milk powder. Preferably, the cryoprotectant that is used in the method of the present disclosure may be a mixture of trehalose, maltodextrin, mannitol and skim milk powder. In the present disclosure, the cryoprotectant may be prepared as an aqueous solution containing the cryoprotectant in an amount of 1 to 90 wt %, 1 to 80 wet %, 1 to 75 wt %, 1 to 70 wt %, 1 to 65 wt %, or 1 to 60 wt %, and may be added to and used in the concentrated lactic acid bacteria cells.

The aqueous cryoprotectant solution may be added and used in an appropriate amount based on the lactic acid bacteria cells. Preferably, it may be added and used in an amount of 0.001 to 99 wt %, 0.01 to 95 wt %, or 0.1 to 95 wt %, based on the weight of the lactic acid bacteria cells.

Coating with Polysaccharide

In the present disclosure, the concentrated lactic acid bacteria may be coated with a polysaccharide to improve the freeze-drying viability, acid resistance and bile resistance of the lactic acid bacteria.

For coating with a polysaccharide, a polysaccharide is added to the concentrated lactic acid bacteria cells, and then mixed and homogenized. Preferably, an aqueous polysaccharide solution containing a polysaccharide may be used.

In the present disclosure, a polysaccharide that may be used for polysaccharide coating of the lactic acid bacteria may be one or more selected from the group consisting of gums, water-soluble dietary fiber, indigestible maltodextrin, insoluble dietary fiber, starch, Levan, and resistant starch. The gums may be one or more selected from the group consisting of xanthan gum, Arabic gum, guar gum, gellan gum, Karaya gum, and locust bean gum. The water-soluble dietary fiber may be polydextrose, glucomannan, β-glucan, pectin, or alginic acid. The insoluble dietary fiber may be chicory extract powder, cellulose, hemicellulose, lignin, or inulin.

According to one embodiment of the present disclosure, the polysaccharide that is used for polysaccharide coating may be a mixture of xanthan gum and cellulose.

In the present disclosure, the polysaccharide coating may be performed by preparing an aqueous polysaccharide solution containing the polysaccharide in an amount of 1 to 80 wt %, 1 to 75 wt %, 1 to 70 wt %, 1 to 65 wt %, 1 to 60 wt %, or 1 to 50 wt %, and adding the prepared aqueous polysaccharide solution to the concentrated lactic acid bacteria cells, followed by mixing and homogenization.

The aqueous polysaccharide solution may be added and used in an appropriate amount based on the weight of the lactic acid bacteria cells. Preferably, it may be added and used in an amount of 0.001 to 99 wt %, 0.01 to 95 wt %, or 0.1 to 95 wt %, based on the weight of the lactic acid bacteria cells.

Freeze-Drying

As described above, the lactic acid bacteria cells obtained by adding the cryoprotectant and polysaccharide components to the protein-coated lactic acid bacteria cells, followed by mixing and homogenization, are freeze-dried.

In accordance with another aspect of the present disclosure, there are provided lactic acid bacteria having a dual coating of protein and polysaccharide, produced by the above-described method.

In accordance with still another aspect of the present disclosure, there is provided a food composition including lactic acid bacteria having a dual coating of protein and polysaccharide, produced by the above-described method.

DETAILED DESCRIPTION

Specific examples described in the present specification are intended to represent exemplary embodiments or examples of the present disclosure, and the scope of the present disclosure is not limited thereby. It will be apparent to those skilled in the art that variations and other uses of the present disclosure do not depart from the scope of the present disclosure as defined in the appended claims of the present specification.

EXAMPLES

Example 1: Measurement of Protein Hydrolysis Rate 1-1. Method for Measurement of Hydrolysis Rate As protein sources that are used for dual coating of lactic acid bacteria, skim milk powder, isolated soy protein (ISP) and a mixture of skim milk powder and isolated soy protein were measured for their rate of hydrolysis induced by protease. Aqueous protein solutions containing different concentrations of each of skim milk powder and isolated soy protein were prepared. Each of the prepared aqueous protein solutions containing different concentrations of each of skim milk powder and isolated soy protein was placed in a reactor equipped with a stirrer, and then suspended and homogenized at 100 RPM at 60° C. Next, the prepared suspensions were adjusted to a pH of 8.2±0.2 by adding 1N NaOH thereto. Tables 1, 2 and 3 below show examples in which suspensions containing different concentrations of each of skim milk powder, isolated soy protein, and skim milk powder+isolated soy protein mixture were prepared.

TABLE 1

Skim milk powder suspension

| Concentration (%) | Substrate amount (kg) | Purified water (l) |
|---|---|---|
| 1.0% | 6 | 594 |
| 2.0% | 12 | 588 |
| 3.0% | 18 | 582 |
| 4.0% | 24 | 576 |
| 5.0% | 30 | 570 |
| 6.0% | 36 | 564 |

TABLE 2

Isolated soy protein (ISP) suspension

| Concentration (%) | Substrate amount (kg) | Purified water (l) |
|---|---|---|
| 0.15% | 0.9 | 599.1 |
| 0.30% | 1.8 | 598.2 |
| 0.45% | 2.7 | 597.3 |
| 0.60% | 3.6 | 596.4 |
| 0.75% | 4.5 | 595.5 |
| 0.90% | 5.4 | 594.6 |

TABLE 3

Skim milk powder + isolated soy protein (ISP) mixture suspension

| Skim milk powder | | Isolated soy protein (ISP) | | |
|---|---|---|---|---|
| Concentration (%) | Substrate amount (kg) | Concentration (%) | Substrate amount (kg) | Purified water (l) |
| 0.5% | 3.0 | 0.10% | 0.6 | Purified water added to 600 l of aqueous solution |
| 1.0% | 6.0 | 0.20% | 1.2 | |
| 1.5% | 9.0 | 0.30% | 1.8 | |
| 2.0% | 12.0 | 0.40% | 2.4 | |

Different concentrations of protease (Alcalase) were added to each of the pH-adjusted suspensions which were then subjected to a hydrolysis reaction at a pH of 6.8 or less for 2 hours. Using "before pH adjustment of each suspension" as a start point (before enzymatic treatment) and using "after 2 hours of the enzymatic reaction" as an endpoint, the hydrolysis rates of the protein sources were measured.

For measurement of the hydrolysis rate of skim milk power, the optical density at 610 nm was measured using a spectrophotometer (SHIMADZU, UV-1280).

Hydrolysis rate $S(\%) = [\Delta OD]/[\text{start-point OD}] \times 100\%$ $[\Delta OD] = \text{start point OD} - \text{endpoint OD}$ For measurement of the hydrolysis rate of isolated soy protein (ISP), first-step centrifugation was performed using a microcentrifuge (Hanil, micro-12) at 13,000 rpm for 15 minutes, the supernatant was discarded, second-step centrifugation for 15 minutes was performed, and then the weight of the precipitate (ppt) was measured.

Hydrolysis rate $I(\%) = [\Delta ppt]/[\text{start-point ppt}] \times 100\%$ $[\Delta ppt] = \text{start point ppt} - \text{endpoint ppt}$ For measurement of the hydrolysis rate of a mixture of skim milk powder and isolated soy protein, the two characteristics (optical density and ppt) were measured and the average value of the measured values was calculated.

Hydrolysis rate $S \& I (\%) = [\text{hydrolysis rate } S + \text{hydrolysis rate } I]/2$

1-2. Results of Hydrolysis Rate Measurement

Table 4 below shows the results of measuring the hydrolysis rate of the skim milk powder depending on the concentration of the skim milk powder and the concentration of the enzyme.

TABLE 4

Results of measuring the hydrolysis rate of skim milk powder depending on the concentrations of skim milk powder and protease

| | Skim | | | | | |
|---|---|---|---|---|---|---|
| Enzyme | 1.0% | 2.0% | 3.0% | 4.0% | 5.0% | 6.0% |
| 0.001% | 90.9% | 75.4% | 73.2% | 68.9% | 65.4% | 59.4% |
| 0.002% | 91.9% | 78.7% | 75.6% | 72.1% | 69.7% | 66.7% |
| 0.003% | 92.1% | 85.0% | 80.6% | 76.2% | 73.9% | 71.6% |
| 0.004% | 92.7% | 88.2% | 86.1% | 85.3% | 80.4% | 76.4% |
| 0.005% | 93.4% | 91.0% | 87.9% | 86.9% | 84.2% | 81.9% |

Concentration: based on skim milk powder solution, w/w %.

Enzyme used: protease (product name: Alcalase 2.4L FG, manufactured by Novozymes A/S Denmark).

From the experimental results, it was confirmed that the hydrolysis rate of the skim milk powder at the same enzyme concentration decreased as the concentration of the skim milk powder increased, and the hydrolysis rate of the skim milk powder increased as the concentration of the enzyme increased.

Table 5 below shows the results of measuring the hydrolysis rate of the isolated soy protein depending on the concentration of the isolated soy protein and the concentration of the enzyme.

TABLE 5

Results of measuring the hydrolysis rate of isolated soy protein depending on the concentrations of isolated soy protein and protease

| | ISP | | | | | |
|---|---|---|---|---|---|---|
| Enzyme | 0.15% | 0.30% | 0.45% | 0.60% | 0.75% | 0.90% |
| 0.005% | 81.6% | 75.9% | 68.1% | 62.7% | 53.3% | 46.8% |
| 0.010% | 82.4% | 77.3% | 71.1% | 65.4% | 58.6% | 50.3% |
| 0.015% | 83.7% | 78.9% | 74.0% | 68.6% | 62.7% | 55.5% |
| 0.020% | 84.1% | 80.0% | 77.9% | 72.6% | 66.3% | 60.7% |
| 0.025% | 85.6% | 81.9% | 79.1% | 74.9% | 69.9% | 66.3% |

Concentration: based on isolated soy protein (ISP) solution, w/w %

Enzyme used: protease (product name: Alcalase 2.4L FG, manufactured by Novozymes A/S Denmark).

It was confirmed that the hydrolysis rate of the isolated soy protein at the same enzyme concentration decreased as the concentration of the isolated soy protein increased, and the hydrolysis rate of the isolated soy protein increased as the concentration of the enzyme increased.

Table 6 below shows the results of measuring the hydrolysis rate depending on the concentration of the mixture of skim milk powder and isolated soy protein.

TABLE 6

Results of measuring the hydrolysis rate depending on the
concentration of the mixture of skim milk powder and isolated
soy protein and the concentration of the enzyme

| | ISP | | | |
|---|---|---|---|---|
| Skim | 0.10% | 0.20% | 0.30% | 0.40% |
| 0.5% | 92.7% | 91.8% | 90.6% | 88.8% |
| 1.0% | 88.4% | 87.2% | 86.3% | 85.1% |
| 1.5% | 84.6% | 83.7% | 82.6% | 80.4% |
| 2.0% | 80.1% | 78.9% | 77.6% | 76.8% |

Concentration: based on the solution of the mixture of skim milk powder and isolated soy protein, w/w %;
Enzyme used: 0.015% protease (product name: Alcalase 2.4L FG, manufactured by Novozymes A/S Denmark).

It was confirmed that the hydrolysis rate at the same enzyme concentration decreased as the concentration of the mixture of skim milk powder and isolated soy protein increased. In addition, at the same enzyme concentration, the hydrolysis rate of the isolated soy protein in the mixture was higher than when the isolated soy protein was used alone.

Example 2: Measurement of Culturability Depending on Hydrolysis Rate of Protein 2-1: Experiment on Culturability Depending on Concentration-Dependent Hydrolysis Rate of Skim Milk Powder In the aqueous protein hydrolysate solution prepared in Example 1, 30 kg of mixed lactose, 6 kg of soy peptone, 12 kg of yeast extract, 1.2 kg of potassium phosphate dibasic, 120 g of magnesium sulfate, 600 g of L-ascorbic acid, 240 g of L-glutamic acid and 600 g of polysorbate-80 were dissolved to a final volume of 1,200 L. The resulting solution was sterilized using a heat exchanger (Alfalaval, Sweden) at a temperature of 130° C. and a flow rate of 1,850 l/hr and transferred to a 1.2-KL-volume anaerobic fermentation tube. Next, 5 L of *Streptococcus thermophilus* CBT ST3 as a starter was inoculated into the solution and then fermented for 13 hours while maintaining the pH at 6.0 with ammonia. After fermentation, the culturability of the lactic acid bacteria depending on the concentration-dependent hydrolysis rate of the skim milk powder and on the concentration of protease was measured. For measurement of the culturability of the lactic acid bacteria, 1 ml of the culture was taken in 9 ml of dilution water and vortexed, and then the number of viable cells was analyzed by the decimal dilution method. The results of the measurement are shown in Table 7 below.

Figure 1:
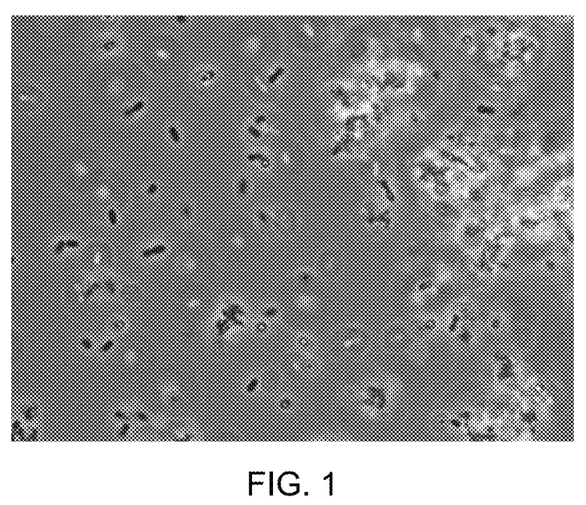
FIG. 1 is a microscopic photograph of a culture of *Streptococcus thermophilus* CBT ST3 (6.0% skim milk powder and 0.003% protease).

From the experimental results shown in Table 7 above, it was confirmed that when the skim milk powder and the protease were used at concentrations of 2% or higher and 0.003% or higher, respectively, excellent culturability could be ensured. At the skim milk powder concentration that was increased to exceed a certain level, the culturability tended to decrease rather than increase, as the proportion of the skim milk powder not degraded by the enzyme increased. As can be seen in a microscopic photograph of FIG. 1, these results were presumed to be because the hydrophobicity of the culture was increased due to an increase in the amount of the non-degraded, non-covalently bonded hydrophobic water-semisoluble peptide, and thus the lactic acid bacteria agglomerated and were not easily divided.

2-2: Experiment on Culturability Depending on Concentration-Dependent Hydrolysis Rate of Isolated Soy Protein Like the case of the skim milk powder, in the hydrolysate solution obtained in Example 1, 24 kg of glucose, 6 kg of soy peptone, 18 kg of yeast extract, 1.2 kg of sodium acetate, 1.2 kg of potassium citrate, 120 g of magnesium sulfate, 1.8 kg of L-cysteine hydrochloride, 600 g of L-ascorbic acid and 1.2 kg of polysorbate-80 were dissolved to a final volume of 1,200 L. The resulting solution was sterilized using a heat exchanger (Alfalaval, Sweden) at a temperature of 130° C. and a flow rate of 1,850 t/hr and transferred to a 1.2-KL-volume anaerobic fermentation tube. Next, 5 L of *Bifidobacterium breve* CBT BR3 as a starter was inoculated into the solution, and then fermented for 14 hours while maintaining the pH at 6.5 with ammonia. After fermentation, the culturability of the lactic acid bacteria depending on the concentration-dependent hydrolysis rate of the isolated soy protein and on the concentration of protease was measured. For measurement of the culturability of the lactic acid bacteria, 1 ml of the culture was taken in 9 ml of dilution water and vortexed, and then the number of viable cells was analyzed by the decimal dilution method. The results of the measurement are shown in Table 8 below.

TABLE 7

Experimental results for the culturability of *Streptococcus thermophilus*
CBT ST3 (KCTC 11870BP) depending on the concentration-dependent hydrolysis
rate of skim milk powder and on the concentration of protease

| | Skim | | | | | |
|---|---|---|---|---|---|---|
| Enzyme | 1.0% | 2.0% | 3.0% | 4.0% | 5.0% | 6.0% |
| 0.001% | 4.9E+09 | 7.1E+09 | 7.4E+09 | 7.3E+09 | 7.0E+09 | 6.7E+09 |
| 0.002% | 5.0E+09 | 7.4E+09 | 7.6E+09 | 7.5E+09 | 7.2E+09 | 6.9E+09 |
| 0.003% | 5.2E+09 | 8.3E+09 | 8.2E+09 | 8.3E+09 | 7.7E+09 | 7.1E+09 |
| 0.004% | 5.2E+09 | 8.2E+09 | 8.3E+09 | 8.2E+09 | 8.2E+09 | 7.4E+09 |
| 0.005% | 5.3E+09 | 8.3E+09 | 8.4E+09 | 8.3E+09 | 8.3E+09 | 7.6E+09 |

TABLE 8

Results of measuring the culturability of *Bifidobacterium breve* CBT
BR3 (KCTC 12201BP) depending on the concentration-dependent hydrolysis
rate of isolated soy protein and on the concentration of protease

|  | ISP | | | | | |
|---|---|---|---|---|---|---|
| Enzyme | 0.15% | 0.30% | 0.45% | 0.60% | 0.75% | 0.90% |
| 0.005% | 6.0E+09 | 8.0E+09 | 8.9E+09 | 9.3E+09 | 7.8E+09 | 6.9E+09 |
| 0.010% | 6.1E+09 | 8.1E+09 | 9.0E+09 | 9.4E+09 | 8.3E+09 | 7.4E+09 |
| 0.015% | 6.3E+09 | 8.2E+09 | 9.3E+09 | 9.4E+09 | 9.3E+09 | 8.2E+09 |
| 0.020% | 6.3E+09 | 8.2E+09 | 9.3E+09 | 9.4E+09 | 9.1E+09 | 8.0E+09 |
| 0.025% | 6.4E+09 | 8.4E+09 | 9.4E+09 | 9.5E+09 | 9.5E+09 | 7.9E+09 |

Figure 2:
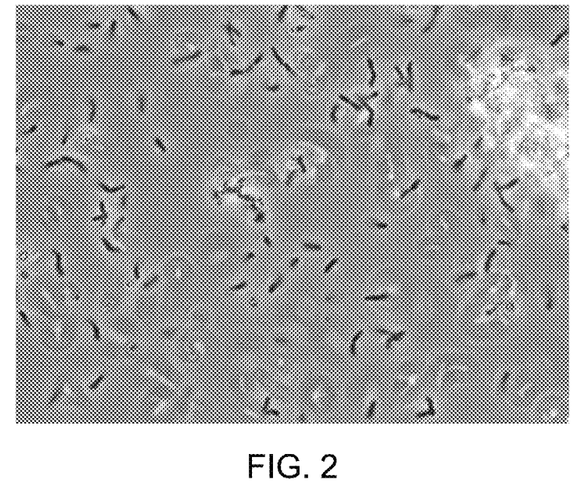
FIG. 2 is a microscopic photograph of a culture of *Bifidobacterium breve* CBT BR3 (0.90% isolated soy protein and 0.015% protease).

From the experimental results shown in Table 8 above, it was confirmed that when the isolated soy protein and the protease were used at concentrations of 0.45% or higher and 0.015% or higher, respectively, excellent culturability could be ensured. At the isolated soy protein concentration that was increased to exceed a certain level, the culturability tended to slightly decrease rather than increase, as the proportion of the isolated soy protein not degraded by the enzyme increased. As can be seen in a microscopic photograph of FIG. 2, these results were presumed to be because the hydrophobicity of the culture was increased due to an increase in the amount of the non-degraded water-semisoluble peptide, and thus the lactic acid bacteria agglomerated and were not easily divided.

2-3: Experiment on Culturability Depending on Concentration-Dependent Hydrolysis Rate of Mixture of Skim Milk Powder and Isolated Soy Protein In the hydrolysate solution of the mixture of skim milk powder and isolated soy protein, prepared in Example 1, 36 kg of crystalline fructose, 36 kg of yeast extract, 2.4 kg of potassium phosphate dibasic, 6 kg of sodium acetate, 1.2 kg of magnesium sulfate, 6 g of manganese sulfate, 1.2 kg of L-cysteine hydrochloride, 1.2 kg of L-ascorbic acid, 2.4 kg of polysorbate-80 and 7.2 kg of refined salt were dissolved to a final volume of 1,200 L. The resulting solution was sterilized using a heat exchanger (Alfalaval, Sweden) at a temperature of 130° C. and a flow rate of 1,850 l/hr and transferred to a 1.2-KL-volume anaerobic fermentation tube. Next, 5 L of *Lactobacillus acidophilus* CBT LA1 as a starter was inoculated into the solution, and then fermented for 20 hours while maintaining the pH at 5.5 with ammonia. After fermentation, the culturability of the lactic acid bacteria depending on the concentration-dependent hydrolysis rate of the mixture of skim milk powder and isolated soy protein was measured. For measurement of the culturability of the lactic acid bacteria, 1 ml of the culture was taken in 9 ml of dilution water and vortexed, and then the number of viable cells was analyzed by the decimal dilution method. The results of the measurement are shown in Table 9 below.

TABLE 9

Results of measuring the culturability of *Lactobacillus acidophilus*
CBT LA1(KCTC 11906BP) depending on the concentration-
dependent hydrolysis rate of the mixture of skim milk
powder and isolated soy protein (ISP)

|  | ISP | | | |
|---|---|---|---|---|
| Skim | 0.10% | 0.20% | 0.30% | 0.40% |
| 0.5% | 5.9E+09 | 6.1E+09 | 6.4E+09 | 6.3E+09 |
| 1.0% | 6.2E+09 | 6.3E+09 | 7.2E+09 | 6.8E+09 |
| 1.5% | 6.4E+09 | 7.0E+09 | 8.2E+09 | 7.2E+09 |
| 2.0% | 6.8E+10 | 7.1E+09 | 8.1E+09 | 6.8E+09 |

Figure 3:
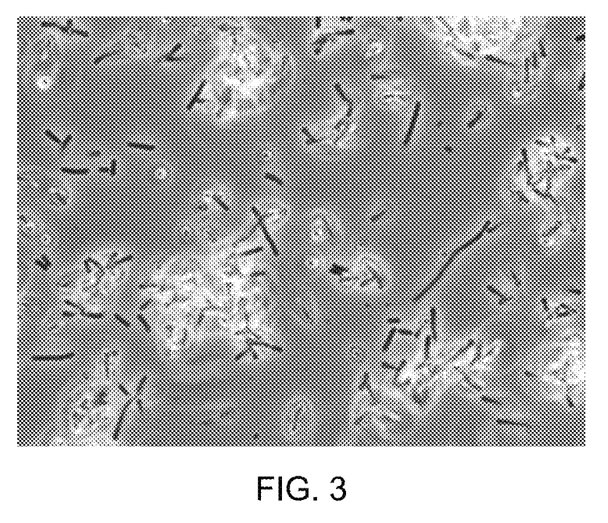
FIG. 3 is a microscopic photograph of a culture of *Lactobacillus acidophilus* CBT LA1 (2.0% skim milk powder, 0.90% isolated soy protein, and 0.015% protease).
Figure 4:
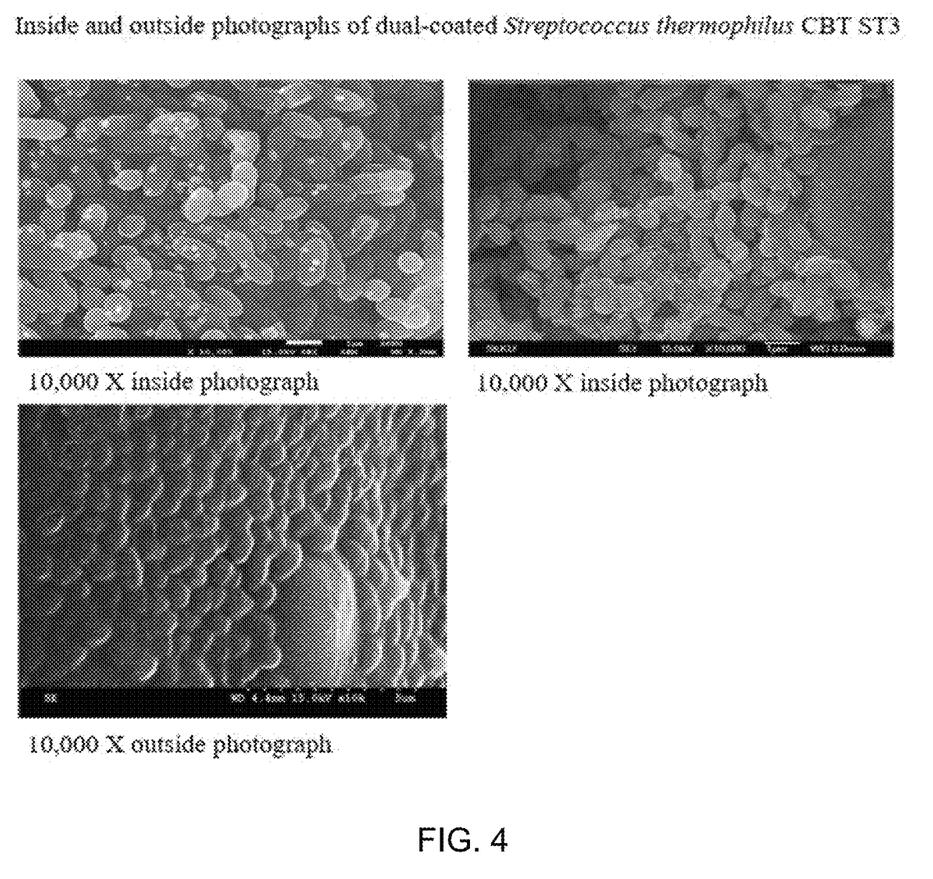
FIG. 4 is a SEM photograph of *Streptococcus thermophilus* CBT ST3 cells dual-coated according to a method of the present disclosure.
Figure 5:
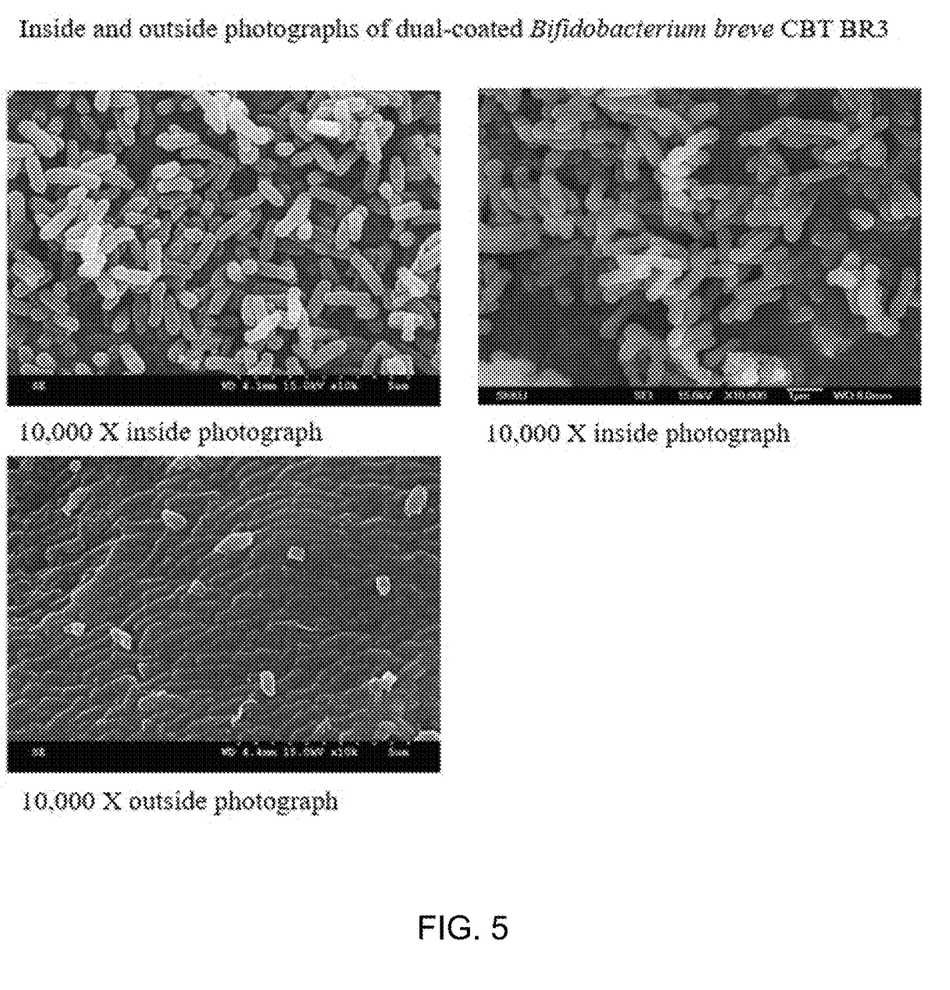
FIG. 5 is a SEM photograph of *Bifidobacterium breve* CBT BR3 cells dual-coated according to a method of the present disclosure.
Figure 6:
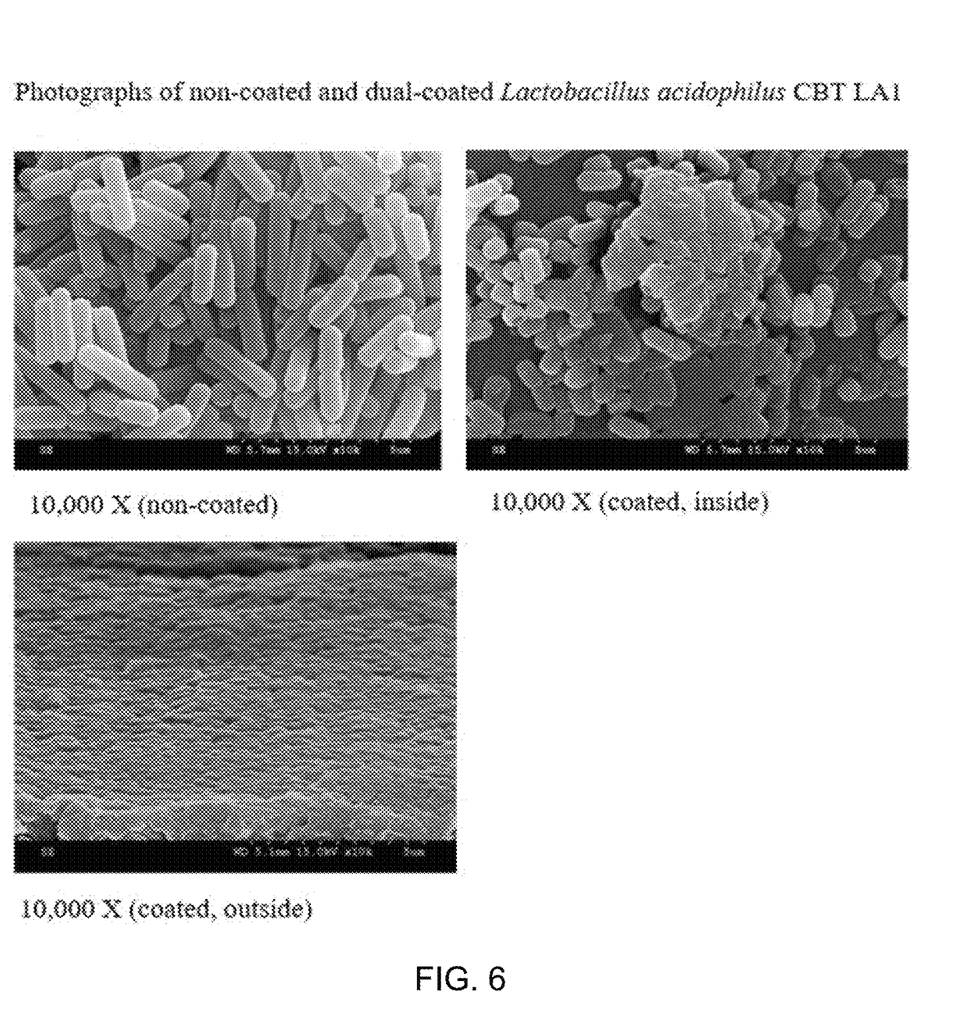
FIG. 6 is a SEM photograph of *Lactobacillus acidophilus* CBT LA1 cells dual-coated according to a method of the present disclosure.

From the experimental results shown in Table 9 above, it was confirmed that when the skim milk powder and the isolated soy protein were used as a mixture at concentrations of 1.5% or higher and 0.3% or higher, respectively, excellent culturability could be ensured. At the mixture concentration that was increased to exceed a certain level, the culturability tended to decrease rather than increase. As can be seen in a microscopic photograph of FIG. 3, these results were presumed to be because the hydrophobicity of the culture was increased due to an increase in the amount of the non-degraded water-semisoluble peptide, and thus the lactic acid bacteria agglomerated and were not easily divided.

Example 3: Measurement of Freeze-Drying Viability Depending on Protein Hydrolysis Rate 3-1: Experiment on Freeze-Drying Viability Depending on Concentration-Dependent Hydrolysis Rate of Skim Milk Powder The fermentation broth obtained in Example 2-1 above was centrifuged using a tubular type high-speed centrifuge (RPM: 15,000 or more, and G-force: 13,200 or more) at a flow rate of 4.0 l/min, and the cells coated with the remaining protein component were recovered by precipitation. 10 L of an aqueous cryoprotectant solution including 3 kg of trehalose, 1 kg of maltodextrin, 1 kg of mannitol and 1 kg of skim milk powder was sterilized by autoclaving and prepared, and 10 L of an aqueous polysaccharide solution obtained by dissolving 20 g of xanthan gum and 20 g of cellulose was sterilized by autoclaving and prepared. Then, the recovered cells and the prepared aqueous cryoprotectant solution and aqueous polysaccharide solution were homogenized by stirring at 200 RPM in a vertical mixer equipped with a whipper. Next, the homogenized mixture was frozen rapidly in a pre-freezer at −40° C., and then the freeze dryer shelf temperature was elevated stepwise from 0° C. by a rate of 10° C./2 hour, and then the mixture was finally freeze-dried at 37° C. In the process of hydrolysis with the protease, the remaining water-semisoluble protein component formed a protein coating on the cells, and the xanthan gum and cellulose polysaccharide components formed a cluster having a very dense structure by binding between the cells. As this time, as the amount of the water-semisoluble peptide was higher than a certain amount, the culturability of the lactic acid bacteria was reduced while the lactic acid bacteria tended to agglomerate. In addition, a suitable amount of the water-semisoluble peptide exhibited excellent freeze-drying viability, accelerated stability, acid resistance and bile resistance by protecting the cells from heat applied during the freeze-drying process. The results of the experiment are shown in Table 10 below.

TABLE 10

Experimental results for the freeze-drying viability of *Streptococcus thermophilus* CBT ST3 (KCTC 11870BP) depending on the concentration-dependent hydrolysis rate of skim milk powder and on the concentration of protease

| Enzyme | Skim | | | | | |
|---|---|---|---|---|---|---|
| | 1.0% | 2.0% | 3.0% | 4.0% | 5.0% | 6.0% |
| 0.001% | 57.7% | 72.9% | 63.8% | 60.3% | 59.0% | 58.1% |
| 0.002% | 56.2% | 73.4% | 65.6% | 62.9% | 59.6% | 58.8% |
| 0.003% | 55.9% | 81.5% | 67.1% | 64.4% | 60.7% | 59.6% |
| 0.004% | 54.5% | 71.5% | 68.6% | 67.0% | 64.3% | 61.1% |
| 0.005% | 53.1% | 69.0% | 70.3% | 67.7% | 65.2% | 63.9% |

Freeze-drying viability (%): the viability after the freeze-drying process was determined in view of the viable cell number and weight before and after freeze-drying.

[Number of viable cells per g after freeze-drying×
weight (g) after freeze-drying]/[number of
viable cells per g before freeze-drying×weight
(g) before freeze-drying]×100%

As shown in Table 10 above, a skim milk powder concentration of 2% and a protease concentration of 0.003% showed the best freeze-drying viability (81.5%). As the skim milk powder concentration increased, the hydrolysis rate tended to decrease and the freeze-drying viability tended to decrease. It was confirmed that a certain amount of the non-degraded water-semisoluble peptide reduced protein denaturation caused by a physical factor applied to the cells and improved the freeze-drying viability. The results of measurement of the culturability and the freeze-drying viability indicated that both the culturability and the freeze-drying viability were excellent when treated with 2.0% skim milk powder and 0.003% enzyme.

3-2: Experiment on Freeze-Drying Viability Depending on Concentration-Dependent Hydrolysis Rate of Isolated Soy Protein According to the experimental method described in Example 3-1, an experiment on freeze-drying viability depending on the concentration-dependent hydrolysis rate of isolated soy protein was performed using the fermentation broth obtained in Example 2-2. The results of the experiment are shown in Table 11 below.

TABLE 11

Experimental results for the freeze-drying viability of *Bifidobacterium breve* CBT BR3(KCTC 12201BP) depending on the concentration-dependent hydrolysis rate of isolated soy protein and on the concentration of protease

| Enzyme | ISP | | | | | |
|---|---|---|---|---|---|---|
| | 0.15% | 0.30% | 0.45% | 0.60% | 0.75% | 0.90% |
| 0.005% | 55.3% | 64.9% | 77.1% | 63.2% | 60.4% | 58.6% |
| 0.010% | 57.9% | 67.1% | 78.9% | 69.7% | 63.2% | 61.1% |

TABLE 11-continued

Experimental results for the freeze-drying viability of *Bifidobacterium breve* CBT BR3(KCTC 12201BP) depending on the concentration-dependent hydrolysis rate of isolated soy protein and on the concentration of protease

| Enzyme | ISP | | | | | |
|---|---|---|---|---|---|---|
| | 0.15% | 0.30% | 0.45% | 0.60% | 0.75% | 0.90% |
| 0.015% | 62.3% | 68.1% | 85.2% | 70.4% | 67.6% | 64.8% |
| 0.020% | 65.9% | 69.6% | 76.1% | 69.6% | 65.8% | 63.1% |
| 0.025% | 69.4% | 70.1% | 75.4% | 68.4% | 64.1% | 61.1% |

Freeze-drying viability (%): the viability after the freeze-drying process was determined in view of the viable cell number and weight before and after freeze-drying.

[number of viable cells per g after freeze-drying×
weight (g) after freeze-drying]/[number of
viable cells per g before freeze-drying×weight
(g) before freeze-drying]×100%

As shown in Table 11 above, an isolated soy protein concentration of 0.45% and a protease concentration of 0.015% showed the best freeze-drying viability (85.2%). As the isolated soy protein concentration increased, the hydrolysis rate tended to decrease and the freeze-drying viability tended to decrease. It was confirmed that a certain amount of the non-degraded water-semisoluble peptide reduced protein denaturation caused by a physical factor applied to the cells and improved the freeze-drying viability. The results of measurement of the culturability and the freeze-drying viability indicated that both the culturability and the freeze-drying viability were excellent when treated with 0.45% isolated soy protein and 0.015% enzyme.

3-3: Experiment on Freeze-Drying Viability Depending on Concentration-Dependent Hydrolysis Rates of Skim Milk Powder and Isolated Soy Protein According to the experimental method described in Example 3-1, an experiment on freeze-drying viability depending on the concentration-dependent hydrolysis rates of skim milk powder and isolated soy protein was performed using the fermentation broth obtained in Example 2-3. The results of the experiment are shown in Table 12 below.

TABLE 12

Freeze-drying viability of *Lactobacillus acidophilus* CBT LA1 (KCTC 11906BP) depending on the concentration-dependent hydrolysis rates of skim milk powder and isolated soy protein

| Skim | ISP | | | |
|---|---|---|---|---|
| | 0.10% | 0.20% | 0.30% | 0.40% |
| 0.5% | 57.7% | 59.9% | 66.2% | 62.9% |
| 1.0% | 63.8% | 65.3% | 71.6% | 67.6% |
| 1.5% | 70.1% | 73.0% | 83.1% | 70.3% |
| 2.0% | 68.8% | 70.1% | 74.2% | 68.6% |

* Freeze-drying viability (%): the viability after the freeze-drying process was determined in view of the viable cell number and weight before and after freeze-drying.

[Number of viable cells per g after freeze-drying×
weight (g) after freeze-drying]/[number of
viable cells per g before freeze-drying×weight
(g) before freeze-drying]×100%

As shown in Table 12 above, when a mixture of 1.5% skim milk powder and 0.3% isolated soy protein was used, the best freeze-drying viability (83.1%) could be obtained. As the mixture concentration increased, the hydrolysis rate tended to decrease and the freeze-drying viability tended to decrease. It was confirmed that a certain amount of the non-degraded water-semisoluble peptide reduced protein denaturation caused by a physical factor applied to the cells and improved the freeze-drying viability. The results of measurement of the culturability and the freeze-drying viability indicated that both the culturability and the freeze-drying viability were excellent when treated with a mixture of 1.5% skim milk powder and 0.3% isolated soy protein.

Example 4: Experiment on Accelerated Stability, Acid Resistance and Bile Resistance by Dual Coating An experiment was performed on the accelerated stability, acid resistance and bile resistance of non-coated lactic acid bacteria, lactic acid bacteria coated with protein alone, and dual-coated lactic acid bacteria. The results of the experiment are shown in Table 13 below.

TABLE 13

Experimental results for accelerated stability, acid resistance and bile resistance depending on non-coating, protein coating and polysaccharide coating

| | Strain | | | | | | | |
|---|---|---|---|---|---|---|---|---|
| | CBT ST3 | | | | CBT BR3 | | | |
| | Protein hydrolysis conditions | | | | | | | |
| | Not used | | 2% skim milk powder + 0.003% enzyme | | Not used | | 0.45% ISP + 0.015% enzyme | |
| Protein coating | X | X | ○ | ○ | X | X | ○ | ○ |
| Polysaccharide coating (dual coating) | X | CMC-Na, XG | X | CMC-Na, XG | X | CMC-Na, XG | X | CMC-Na, XG |
| Accelerated stability | 19.2% | 38.3% | 54.2% | 85.2% | 12.5% | 33.2% | 44.1% | 65.2% |
| Acid resistance | 35.2% | 52.8% | 70.0% | 90.7% | 23.6% | 51.2% | 69.5% | 88.6% |
| Bile resistance | 30.7% | 50.5% | 70.7% | 91.6% | 26.6% | 51.8% | 56.8% | 83.1% |

CMC-Na: cellulose;
XG: xanthan gum;

Accelerated stability: 1 g of each sample was taken in 9 ml of dilution water and vortexed, and then the initial number of viable cells was analyzed by the decimal dilution method. Additionally, after each sample was incubated at 40° C., the number of viable cells was analyzed once a week for 4 weeks, and the viability relative to the initial number of viable cells was examined.

Acid resistance: 0.1 g of each sample was dissolved in 9.9 ml of MRS broth solution (pH 2.1) corrected with 1M HCl solution, and then the number of viable cells at 0 hour and 2 hours was analyzed while maintaining a temperature of 37° C., and the viability relative to the viability at 0 hour was examined.

Bile resistance: 0.1 g of each sample was dissolved in 9.9 ml of 0.5% oxgall-containing MRS broth solution, and then the number of viable cells at 0 hour and 2 hours was analyzed while maintaining a temperature of 37° C., and the viability relative to the viability at 0 hour was examined.

The results of comparative analysis of non-coated lactic acid bacteria, protein-coated lactic acid bacteria and dual-coated lactic acid bacteria indicated that the dual-coated lactic acid bacteria could exhibit better accelerated stability, acid resistance and bile resistance than the non-coated or single (protein)-coated lactic acid bacteria. Since the rate of death caused by a physical factor applied to the cells is low and the physiologically active function of the lactic acid bacteria cannot be lost, the dual-coated lactic acid bacteria exhibit improved accelerated stability, acid resistance and bile resistance.

As described above, the present disclosure relates to a method of producing lactic acid bacteria dual-coated with protein and polysaccharide by using a protein hydrolysate, and lactic acid bacteria having a dual coating, produced by the method. The lactic acid bacteria having a dual coating of protein and polysaccharide, produced according to the present disclosure, have very excellent dry-freezing viability, acid resistance and bile resistance. Accordingly, the lactic acid bacteria having a dual coating of protein and polysaccharide according to the present disclosure will be very useful for the production of fermented milk, processed milk, fermented soy products, processed foods, functional beverages, functional foods, common foods, etc.

Although the present disclosure has been described in detail with reference to the specific features, it will be apparent to those skilled in the art that this description is only of a preferred embodiment thereof, and does not limit the scope of the present disclosure. Thus, the substantial scope of the present disclosure will be defined by the appended claims and equivalents thereof.

What is claimed is:

1. A method of producing lactic acid bacteria having a dual coating of protein and polysaccharide coatings, the method comprising the steps of:
   (a) treating an aqueous protein solution with a protease, thereby preparing an aqueous protein hydrolysate solution;
   (b) adding a sugar component and a nitrogen source component for lactic acid bacteria culture to the prepared aqueous protein hydrolysate solution, followed by sterilization, and then inoculating and culturing the lactic acid bacteria in the sterilized aqueous solution;
   (c) recovering lactic acid bacteria cells from a fermented lactic acid bacteria culture obtained by the culturing;
   (d) adding an aqueous cryoprotectant solution and an aqueous polysaccharide solution to the recovered lactic acid bacteria cells, followed by mixing and homogenization; and
   (e) freeze-drying the homogenized aqueous lactic acid bacteria cell solution, wherein the hydrolysis rate of the protein in step (a) is:

(i) a percentage value (%) obtained by dividing a DOD value, which is a difference between the optical density (OD) value ("start-point OD") of the aqueous protein solution, measured before treatment with the protease, and the optical density (OD) value ("end-point OD") of the aqueous protein solution, measured after treatment with the protease, by the start-point OD value; or (ii) a percentage value (%) obtained by dividing a Δppt value, which is a difference between the measured weight value ("start-point ppt") of a precipitate, obtained by centrifuging the aqueous protein solution before treatment with the protease, and the measured weight value ("endpoint ppt") of a precipitate, obtained by centrifuging the aqueous protein solution after treatment with the protease, by the start-point ppt value, wherein the protein in step (a) is isolated soy protein (ISP), wherein the concentration of the ISP is 0.45% and the concentration of the protease is 0.015%, wherein the hydrolysis rate of the isolated soy protein is 74.0%, wherein the lactic acid bacteria is *Bifidobacterium breve* CBT BR3 (KCTC 12201 BP).

2. The method of claim 1, wherein the sugar component for lactic acid bacteria culture in step (b) is one or more selected from the group consisting of fructose, sucrose and glucose.

3. The method of claim 1, wherein the nitrogen source component for lactic acid bacteria culture in step (b) is yeast extract or soy peptone.

4. The method of claim 1, wherein the cryoprotectant in step (d) is one or a mixture of two or more selected from the group consisting of trehalose, maltodextrin, mannitol, and skim milk powder.

5. The method of claim 1, wherein the polysaccharide in step (d) is one or more selected from the group consisting of gums, water-soluble dietary fiber, indigestible maltodextrin, insoluble dietary fiber, starch, Levan, and resistant starch.

* * * * *